United States Patent
Conti et al.

(10) Patent No.: US 8,226,723 B2
(45) Date of Patent: Jul. 24, 2012

(54) SELF-RETAINING ARTIFICIAL SPINAL DISC, AND ASSOCIATED METHODS

(75) Inventors: James C. Conti, Galena, MO (US); Elaine R. Strope, Galena, MO (US)

(73) Assignee: Dynatek Laboratories, Inc., Galena, MO (US)

( * ) Notice: Subject to any disclaimer, the term of this patent is extended or adjusted under 35 U.S.C. 154(b) by 642 days.

(21) Appl. No.: 12/313,395

(22) Filed: Nov. 20, 2008

(65) Prior Publication Data

US 2010/0125332 A1     May 20, 2010

(51) Int. Cl.
*A61F 2/44*     (2006.01)
(52) U.S. Cl. .................................... 623/17.16
(58) Field of Classification Search .... 623/17.11–17.16; 264/240, 275
See application file for complete search history.

(56) References Cited

U.S. PATENT DOCUMENTS

| | | | | |
|---|---|---|---|---|
| 4,863,477 A * | 9/1989 | Monson | ..................... | 623/17.12 |
| 545,864 A | 10/1995 | Oka et al. | | |
| 6,736,815 B2 * | 5/2004 | Ginn | ............................. | 606/60 |
| 2005/0055099 A1 | 3/2005 | Ku | | |
| 2005/0154464 A1 * | 7/2005 | Humphreys et al. | ....... | 623/17.16 |
| 2005/0171611 A1 | 8/2005 | Stoy et al. | | |
| 2007/0191957 A1 * | 8/2007 | Anderson et al. | .......... | 623/17.16 |

\* cited by examiner

*Primary Examiner* — Ellen C Hammond
(74) *Attorney, Agent, or Firm* — Lathrop & Gage LLP (57) ABSTRACT

A self-retaining artificial spinal disc is formed of a flexible material and has a peripheral lip or meniscus extending from its top and/or bottom surface. The meniscus/menisci encircle portions of vertebrae adjacent the implant site, to enhance retention of the artificial spinal disc when seated in the spinal column. The meniscus/menisci for example snugly overlie the vertebral portions, and foster a suction seal between the disc and the adjacent vertebrae. The disc may be formed as an integral whole, or as two half-discs joinable by gluing, melting or like methods. In a related method, a self-retaining artificial spinal disc is formed in layers, by pouring and drying measures of liquid disc solution in a mold. A meniscal extension is formed from the disc body. Drugs or salts may be added to the disc layers, for example to provide an artificial spinal disc with time-release antibiotics or a desired porosity.

13 Claims, 7 Drawing Sheets

SELF-RETAINING ARTIFICIAL SPINAL DISC, AND ASSOCIATED METHODS

BACKGROUND

1. Field

This disclosure relates generally to the field of artificial intervertebral discs, and more particularly to an implantable polymeric replacement disc.

2. Description of Related Art

Artificial intervertebral (or spinal) discs are gaining acclaim as a treatment for degenerative disc disease and as a viable alternative to spinal fusion surgery. Substantial research, testing and prototyping has occurred over recent decades, in an effort to develop a replacement disc which is easy to implant and adequately retained in an appropriate orientation once placed, and which imitates the properties and functions of a natural disc. Development efforts have also focused on creating a replacement disc that is flexible (e.g., imitable of the 2-3% flexion of natural discs), accommodating of loading and movement, and which does not impinge or otherwise adversely affect the adjacent vertebrae or spinal nerve roots. Likewise, much consideration has been given to durability and biocompatibility of artificial disc materials, as the artificial disc should ideally be durable enough to function throughout the life of the recipient, without rejection.

Accordingly, prior art artificial discs run the gambit, from rigid implantable devices retained with screws in adjacent vertebrae, to simple sponge-like discs positioned and retained between vertebrae. U.S. Patent Application Publication No. 2005/0055099, by Ku, describes one such artificial disc, which is porous to facilitate tissue ingrowth, both for additional stabilization of the disc and with the aim of allowing the disc, over time, to more closely imitate the functioning of a natural spinal disc. Other solutions combine inflexible and resilient components, for example sandwiching the resilient material between plates made from metal or another similarly rigid material. Often, the rigid plates have external protrusions or spines which are intended to seat into adjacent vertebrae. These sandwich type replacement discs are commonly screwed into adjacent vertebrae or else retained via complex retention brackets, wires, ties, bolts, rivets and the like. Implanting these "fixed" replacement discs thus requires the surgeon to drill into adjacent vertebrae or to use a variety of hardware to otherwise fix the replacement disc to the adjacent vertebrae.

These conventional manners of fixing artificial replacement discs may not only damage the adjacent vertebrae, but also limit spinal flexibility, excessively compress the replacement disc, adversely affect replacement disc durability, increase recipient recovery time and increase the risk of disc rejection by the recipient. Each of these adverse effects may compromise overall health of the recipient, necessitating additional medical treatment and even surgery.

Consequently, there has been movement away from artificial discs which require substantial hardware (e.g., screws, brackets or wires) to mount in place. The early 1990s to present has been marked by a trend toward greater resilience, less rigidity and less surgical attachment to adjacent vertebrae. For example, the aforementioned Ku application and also U.S. Patent Application Publication No. 2005/171611, by Stoy, disclose flexible discs.

The Stoy application particularly discusses a prosthetic disc having parallel layers of hydrogel. The rigidity of the disc is determined by the number of parallel layers fabricated. However, similar to previously discussed replacement discs, the Stoy application discusses the need for at least one rigid layer. It is also complex to manufacture and somewhat cumbersome to implant, because the disc is dehydrated during implantation and then must be hydrated to achieve a desired stiffness to flexibility ratio. A similar artificial disc is disclosed in U.S. Pat. No. 5,458,543, issued to Oka.

The Ku application moves away from the trend of layered artificial discs, disclosing a unitary elastomer which is manufactured with specific chemical properties to substantially replicate the nucleus of a natural spinal disc. However, the Ku disc must be mechanically fixed in place. It is thus provided with a protrusion or appendage extending outward from the flexible portion of the disc, for mechanically fixing to the adjacent vertebrae.

SUMMARY

The disclosed self-retaining artificial spinal disc sufficiently replicates naturally occurring discs and may be implanted without the use of mechanical fasteners, thus overcoming the above-described limitations of the prior art.

In one embodiment, a self-retaining artificial spinal disc includes a disc body formed of a flexible material and having a superior surface and an opposed inferior surface. The disc body sized to fit an implant site between two vertebrae. A meniscus extends from the periphery of the superior or the inferior surface, for encircling a portion of a first of the vertebrae adjacent the implant site, to retain the artificial spinal disc in place.

In one embodiment, a self-retaining artificial spinal disc includes an upper half-disc formed of a flexible material and having an inferior surface, a superior surface and a superior meniscus extending from a periphery of the superior surface. A lower disc half is formed of the flexible material and includes a joining surface for joining to the inferior surface of the upper half-disc. The superior meniscus secures the upper and lower half-discs to a first vertebra adjacent a spinal implant site, when the upper and lower half-discs are joined.

In one embodiment, a method for making a self-retaining artificial spinal disc includes preparing a mold for forming a disc body and pouring a first measure of liquid disc solution into the mold, to form a first disc body layer. The mold is dried and the pouring and drying steps are repeated to form at least one subsequent disc body layer. A meniscal extension of the disc body is formed, and the disc body removed from the mold.

DETAILED DESCRIPTION

Figure 1:
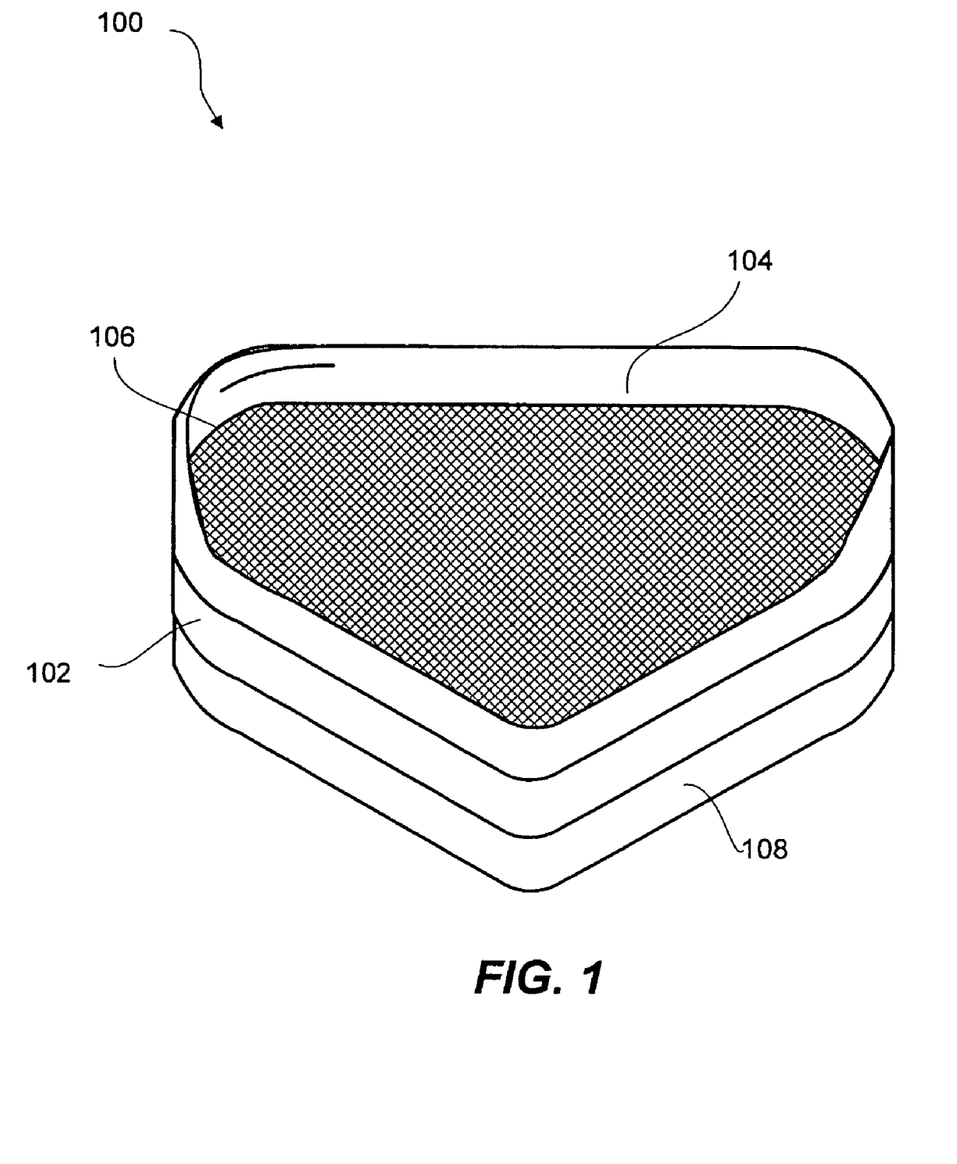
FIG. 1 is a top perspective view of a self-retaining artificial spinal disc, in accord with an embodiment.

FIG. 1 shows a self-retaining artificial spinal disc 100. Disc 100 is made from a material that generally imitates the look and feel of a natural vertebral disc, e.g., formed of an elastomer, a flexible polymer, silicone, a silicone compound, polyurethane and/or the like. It is for example sized and shaped to substantially match a natural vertebral disc, and has one or more characteristics imitable of a natural disc, such as hardness, flexibility, tensile strength, weight, porosity, and compressibility. Consistent with the characteristics of natural vertebral discs, disc 100 for example has a hardness equivalent between about 20 and about 35 on the Shore type A scale.

Disc 100 has a flexible disc body 102, made for example from silicone, a silicone compound, an elastomer or a flexible polymer. A superior edge or lip 104 (hereinafter referred to as a meniscal extension or meniscus 104) extends from a superior disc body face 106 and an inferior edge or lip 108 (hereinafter, meniscal extension or meniscus 108) extends from an inferior disc body face 110 (see FIG. 2).

Disc 100 is specifically dimensioned for insertion and self-retention within an intervertebral space and between adjacent vertebrae, for example in place of natural disc that is removed due to degeneration or trauma. Menisci 104 and 106 are thin but strong peripheral bands that may diminish in thickness as they extend away from disc body faces 106, 110. Menisci 104, 106 may be formed as extensions of the disc body material, e.g., as integral parts of the disc body, during the manufacturing process. For example, a small meniscus may be formed during the manufacturing process when the disc material is molded, as explained herein below with respect to FIG. 3. A small lip or meniscus naturally forms by adhesion of the disc material to the sidewall of the mold. The size of the meniscus can be controlled by utilizing a mold or shaping device specifically configured to allow the meniscus to form around the periphery of the disc body.

In one embodiment, meniscus 104 is formed to encircle and fit snugly around a portion of a vertebra, for example slightly overlapping a bottom portion of a vertebral body that is adjacent and cranial to an implant site within the spinal column. During an implant procedure, meniscus 104 is positioned about the bottom portion of the cranially adjacent vertebral body, and pressure is applied to disc 100 to create a vacuum or suction seal between disc 100 and the cranially adjacent vertebral body (particularly, between superior disc body face 106 and the cranially adjacent vertebral body). Meniscus 108 is likewise formed to snugly encircle a portion of a vertebra, e.g., slightly overlapping a top portion of a vertebral body that is adjacent and caudal to the implant site. Once meniscus 108 is properly positioned about the bottom portion of the caudally adjacent vertebral body, pressure may again be applied to disc 100, or the recipient's spinal column may be manipulated to press against disc 100, to encourage a vacuum or suction seal between disc 100 and the caudally adjacent vertebral body. For example, aided by meniscus 108, a suction seal forms when disc 100 is pressed to inferior disc body face 110. Disc 100 may thus remain securely in place without the screws or other hardware that is necessary to secure prior art replacement discs. Disc 100 may likewise be secured first to the caudally adjacent vertebral body and second to the cranially adjacent vertebral body, or as otherwise preferred by an attending surgeon.

Figure 2:
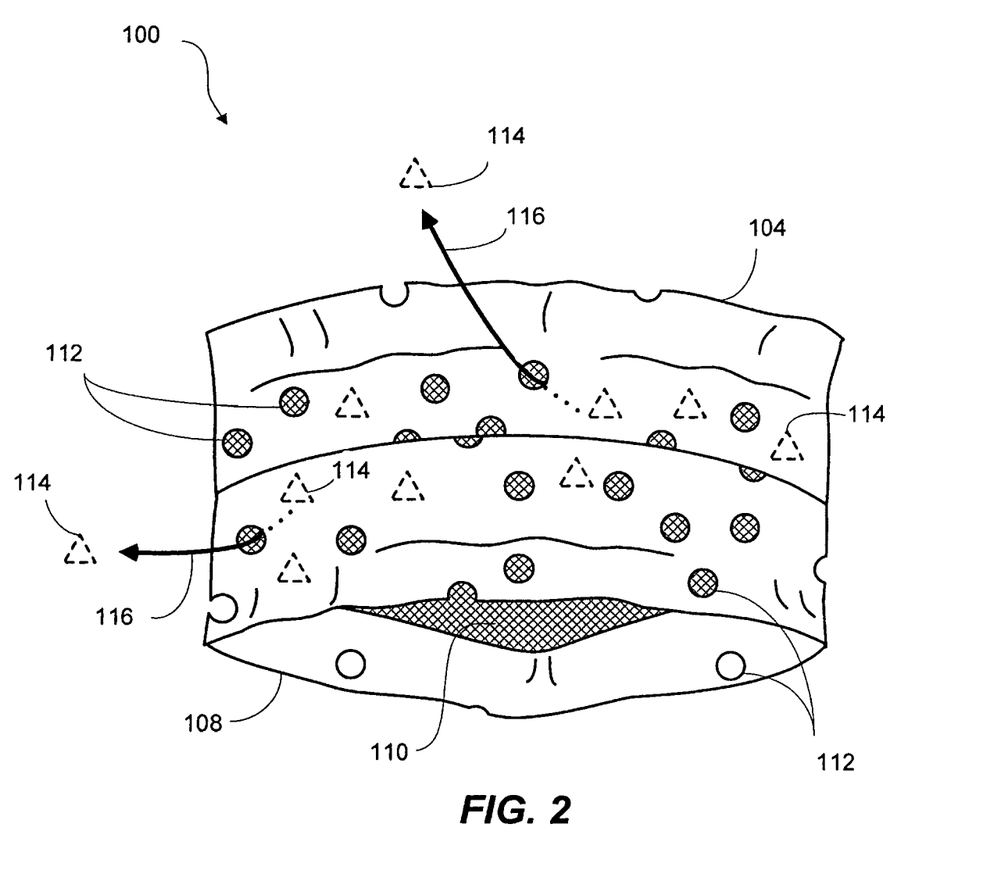
FIG. 2 is a perspective view of the self-retaining artificial spinal disc of FIG. 1, showing exemplary disc porosity in an alternative embodiment.

Self-retention of disc 100 may be enhanced by providing pores 112 in disc 100, as shown in FIG. 2. Disc porosity is for example provided by adding a salt or other solute to the artificial disc material (e.g., silicone, polymer, etc.) prior to hardening. The degree of porosity (and hence the final disc density and overall disc flexibility) may be controlled by controlling the percent solute. Disc density and rigidity are also adjustable by changing the type or properties of the elastomeric material from which the disc is formed; thus, disc 100 may thus be customized to the needs of an individual recipient. For example, a very large or overweight recipient may require a denser, more rigid artificial disc than would a small, slim person. Likewise, a younger person might require a more flexible (e.g., more porous) artificial disc than an older person.

Pores 112 additionally provide portals for tissue ingrowth, enhancing stabilization of disc 100. In one embodiment, disc 100 has a porosity of about 5 to about 20 microns, with a void volume of about 20% to about 30% of overall disc volume. Although disc 100 is made from biocompatible material or materials (such as silicone or a silicone compound) it may be impregnated, coated or infused with anti-rejection, anti-inflammatory and/or antibiotic drugs to further decrease the likelihood of rejection and complications.

In FIG. 2, drugs 114 are indicated by dotted triangles. Drugs 114 may be infused or impregnated into disc body 102 (and/or menisci 104, 108) such that they diffuse out of the implanted disc 100 through pores 112, as shown by directional arrow 116. Drugs 114 may likewise coat the outside of disc body 102 and/or disc body faces 106, 110 and menisci 104, 108, and diffuse off of the implanted disc 100 into the recipient's body. Disc 100 may thus serve as a carrier for time released antibiotics 114 to guard against post-operative infection.

Self-retention may also be enhanced by customizing a disc 100 to a recipient. Although disc 100 may be manufactured in a variety of sizes and with a variety of surface topographies, to fit a range of patient sizes and vertebral shapes, overall disc size and topography may be calibrated and shaped on an individual basis. For example, MRI, tomography or ultrasound may be used to image an existing disc that is to be replaced, an intervertebral implant site and/or vertebral faces adjacent the implant site. The obtained image may be used to customize disc 100 to match the size and shape of the implant site or the existing disc. Disc 100 is flexible; thus, superior and inferior faces 106, 110 may conform to features of adjacent vertebral faces. Conformity may be enhanced by providing faces 106, 110 with subtle undulations or texture. Optionally, faces 106, 110 may be customized to fit topographical features of the adjacent vertebral faces. Protrusions and extensions that are counterparts to extensions and protrusions of the vertebral faces may for example be molded onto faces 106, 110 of a finished artificial disc 100; or faces 106, 110 may be provided with customized topography during formation of disc 100.

Figure 3:
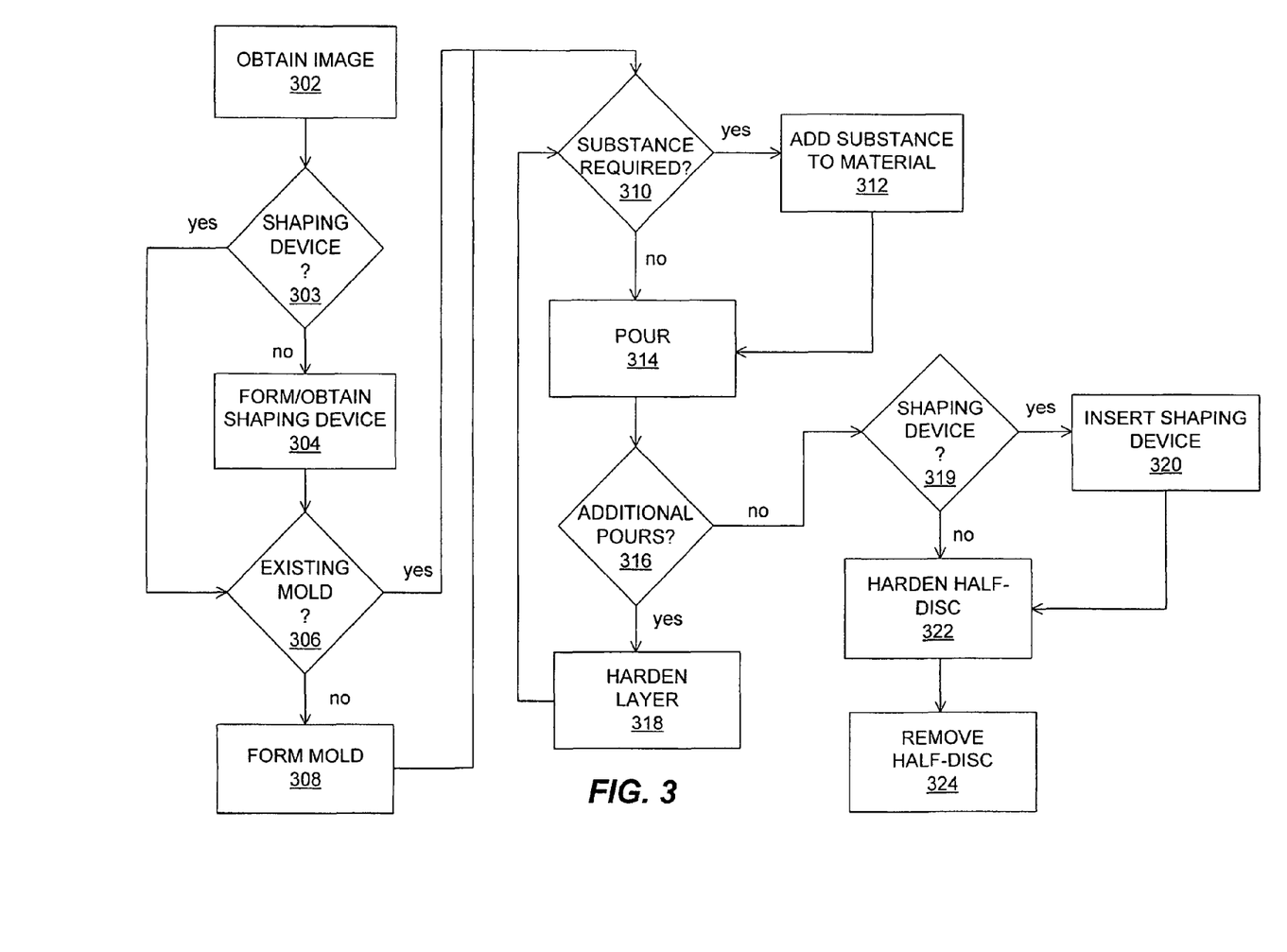
FIG. 3 is a flow chart exhibiting an exemplary method of forming a disc halves, joinable to form an artificial spinal disc as in FIG. 1 or 2.

In one embodiment, a replacement disc 100 is custom cast to fit a recipient's adjacent vertebral bodies, for example with recesses sized to fit corresponding vertebral extrusions, and vice versa. FIG. 3 illustrates one method 300 of forming one half of a customized artificial spinal disc, such as disc 100. In step 302, an image or images of a recipient's spinal column are obtained, for example by MRI, ultrasound, tomography or similar method. The images for example capture a damaged disc that is to be replaced, an intervertebral implant space and a face of at least one vertebral body adjacent the implant site. If a shaping device is to be used, decision 303, the device is obtained or formed in step 304, as desired. The images obtained in step 302 are for example used to diagram the outer surfaces of a vertebra adjacent the implant site, e.g., a cranially adjacent vertebra, and to form the shaping device in imitation of the size and shape of the cranially adjacent vertebra. In one embodiment, the shaping device is a stopper with texture or topography, which is inserted into liquid disc material to create retention-enhancing features on a disc surface. A textured shaping device may be provided to create conformity-enhancing texture on superior and inferior faces of the artificial disc (e.g., faces 106, 110 of disc 100). Alternately or optionally, the shaping device is formed with a topography opposite that of the cranially adjacent vertebral face (e.g., bearing extrusions to fit recessions in the vertebral face, and vice-versa).

If an existing, pre-formed mold complements the size and shape of the intervertebral space or the damaged disc (e.g., specifications of the existing mold match or are suitably close to the size and shape of (a) the intervertebral space to be filled, or (b) the recipient's natural disc, prior to damage), decision 306, a determination is made as to whether a substance is to be added to the artificial disc material, in decision 310. Antibiotic, anti-inflammatory or anti-rejection drugs may be infused or mixed into the artificial disc material, which is for example a liquid or molten elastomeric material. Optionally or additionally, a solute may be mixed into the material to increase porosity, and thus flexibility, of the final artificial half-disc. Likewise, additional chemicals or substances may be added to the material to vary its physical or chemical properties, in order to vary the properties of the half-disc. If desired, such substance or substances are added to the artificial disc material, in step 312. If no substance is to be included in the disc half (if a one-pour process) or the particular layer of the disc half (in a multi-pour process), liquid artificial disc material is poured into the mold, in step 314.

In a multi-pour process (decision 316, described below), between 5 ml and 25 ml of liquid solution may be added to the mold with each pour. The liquid disc material may be a silicone-based compound, a polymer or an elastomer. In one embodiment, the liquid disc material is a 35% solid to solution composition of polydimethylene in zylene. Multi-pour processes may be preferable when the disc material contains zylene, as zylene may become trapped in solution during a single pour process, which can result in unwanted voids in the structure as the zylene dissipates over time.

Returning to decision 306, if specifications of the intervertebral space or the natural disc (damage aside) are not satisfactorily met by a pre-formed mold, a complementary mold is formed, in step 308. The mold is for example formed from aluminum stock and substantially reflects the size and shape of the natural disc that is to be replaced, except that damage to the natural disc is "repaired" in the mold. A mold release material such as polyteflon may be applied to the mold (or to the existing mold of decision 306) prior to pouring the liquid disc material. Forming the mold may include forming a model of a disc (e.g., a healthy disc or the damaged disc with damage "repaired" in the model) and casting the model. The model/mold may be formed slightly larger than the natural disc to allow for formation of a meniscus around the inner periphery of the mold, to accommodate compression, or to allow later alterations to the artificial disc perimeter or surfaces.

If additional pours are desired or required, decision 316, the artificial disc layer is allowed to harden, in step 318. The disc material may be hardened by drying at a relatively low temperature, for example at 90-100° F. for about one to three hours.

Following hardening, a determination is again made as to whether the next material layer should be augmented with drugs, salts or other substances, decision 310. The layer, and any subsequent layers, are augmented, poured and hardened as required (steps 312-316), until the half-disc reaches a suitable thickness. The final half-disc (or disc 100 when formed as a whole) may also be cured by heating to a temperature of about 300° F. for two to five hours.

Forming the half-disc in multiple pouring and hardening steps allows for addition of drugs or other chemicals (e.g., salts or other porosity-enhancing solvents) at virtually any level of the disc. This may facilitate control of drug release and other disc properties. For example, adding one drug added to different levels of the disc may provide time-released pharmaceutical effects as the drug diffuses from the outer and inner layers of the artificial disc and into a patient's body. Likewise, pharmaceutical effects may be selectively controlled by adding different drugs to different layers of the disc. Disc flexibility may also be selectively controlled by varying porosity at different levels of the half-disc, for example by altering the amount of salts or other solutes added to disc layers.

If/when no additional pours are required and if a shaping device is to be used, decision 319, the shaping device is inserted into or placed atop the material, in step 320. In one embodiment, the outer periphery of the stopper is slightly less than the inner circumference of the mold. When the stopper is placed in or on the disc material, the material is displaced upwards between the outer periphery of the stopper and the inner surface of the mold. The displaced disc material creates a meniscus. The circumference of the stopper may be beveled or angled to form a meniscus that decreases in thickness from base to upper edge. Meniscus thickness and overall size may also be affected by the type and amount of release agent used to coat the mold. It is also noted that a meniscus may form naturally as the mold is filled, due to surface tension and the adhesive propensity of the mold material. Thus, a meniscus may be provided even when no shaping device is used in forming the artificial half-disc.

The artificial half-disc is hardened, in step 322, and removed from the mold in step 324. Steps 302-324 are repeated as necessary to form the complementary half of the final artificial spinal disc. In an embodiment, the images obtained in step 302 include images a second vertebral body adjacent the implant site (e.g., the caudally adjacent vertebral body), and may be re-used to form a shaping device complementary to the face of the caudally adjacent vertebral body proximate the implant site. Likewise, the mold used to form the half-disc (e.g., an upper half-disc) may be re-used to form the second (e.g., lower) half-disc, if appropriate. Once formed, the two half-discs are joined back-to back, with menisci facing outward, to form a complete artificial spinal disc. For example, an upper half disc with a meniscus extending from a superior face may join at its inferior face to a superior or joining face of a lower half-disc that has a meniscus extending from its inferior face.

In some cases, it may be sufficient to provide an artificial disc with a single meniscus, oriented generally upward or downward respective to the recipient's spine. In such case, method 300 may be performed using a mold that forms a complete discs with a meniscus on one side, in place of the half-disc molds discussed above. A unitary disc with one or two menisci may also be formed by machining the meniscus or menisci from a solid piece of replacement disc material. This may allow for precise control of meniscus thickness and length. For example, an artificial disc is formed by pouring liquid disc solution into a mold and, after drying the mold, cutting away a portion of the superior and/or inferior surfaces of the disc while leaving an annular strip of meniscus material about the periphery.

Figure 4:
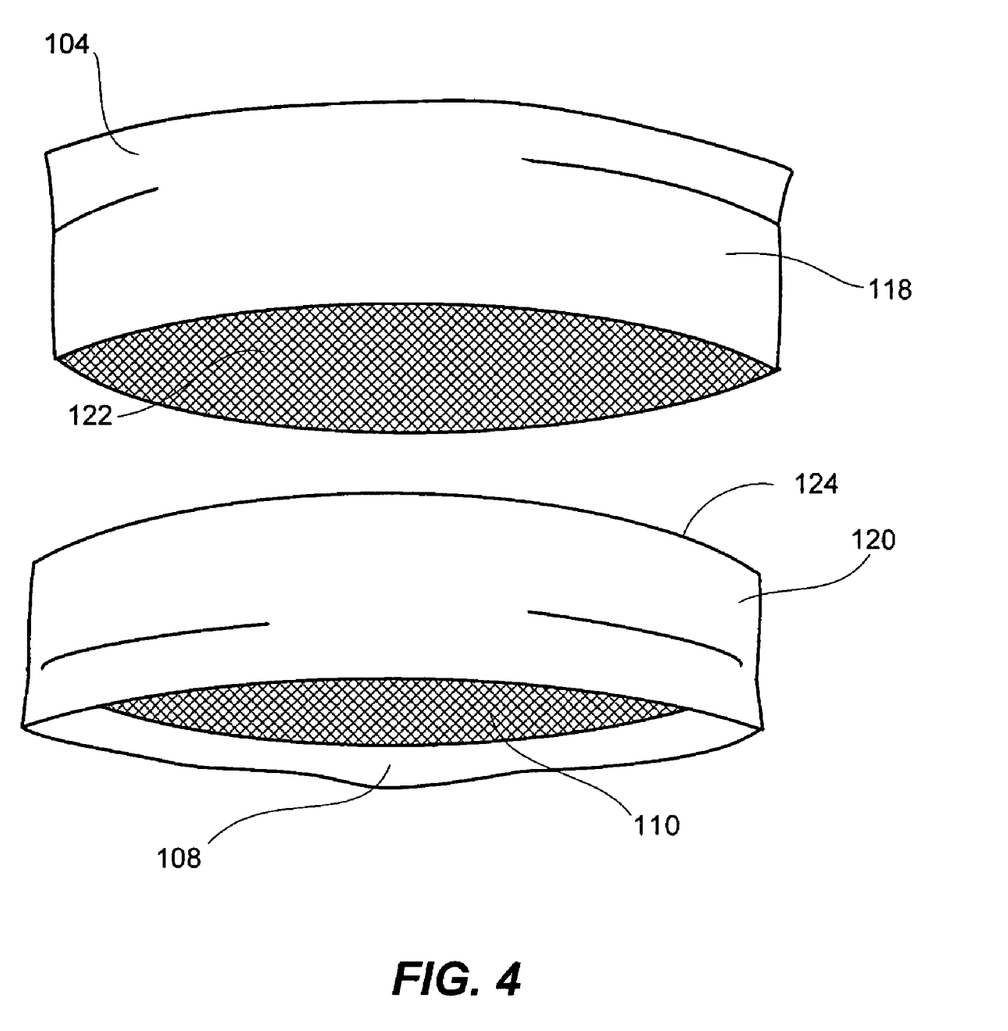
FIG. 4 is a perspective view of upper and lower disc halves, as may be formed by the method of FIG. 3.

FIG. 4 shows upper and lower half-discs 118 and 120. Half-discs 118 and 120 are for example formed as described with respect to method 300. Upper half-disc 118 has an inferior surface 122, for fitting to a superior or joining surface 124 of lower half-disc 120. Upper and lower half-discs 118, 120 are for example glued, melted or otherwise firmly fixed together at bottom surface 122 and joining surface 124. Bottom and joining surfaces 122, 124 may be flat, as shown, or they may be formed with complementary lock-and-key features to aid in joining upper and lower half-discs 118, 120, as shown in FIG. 5.

Figure 5:
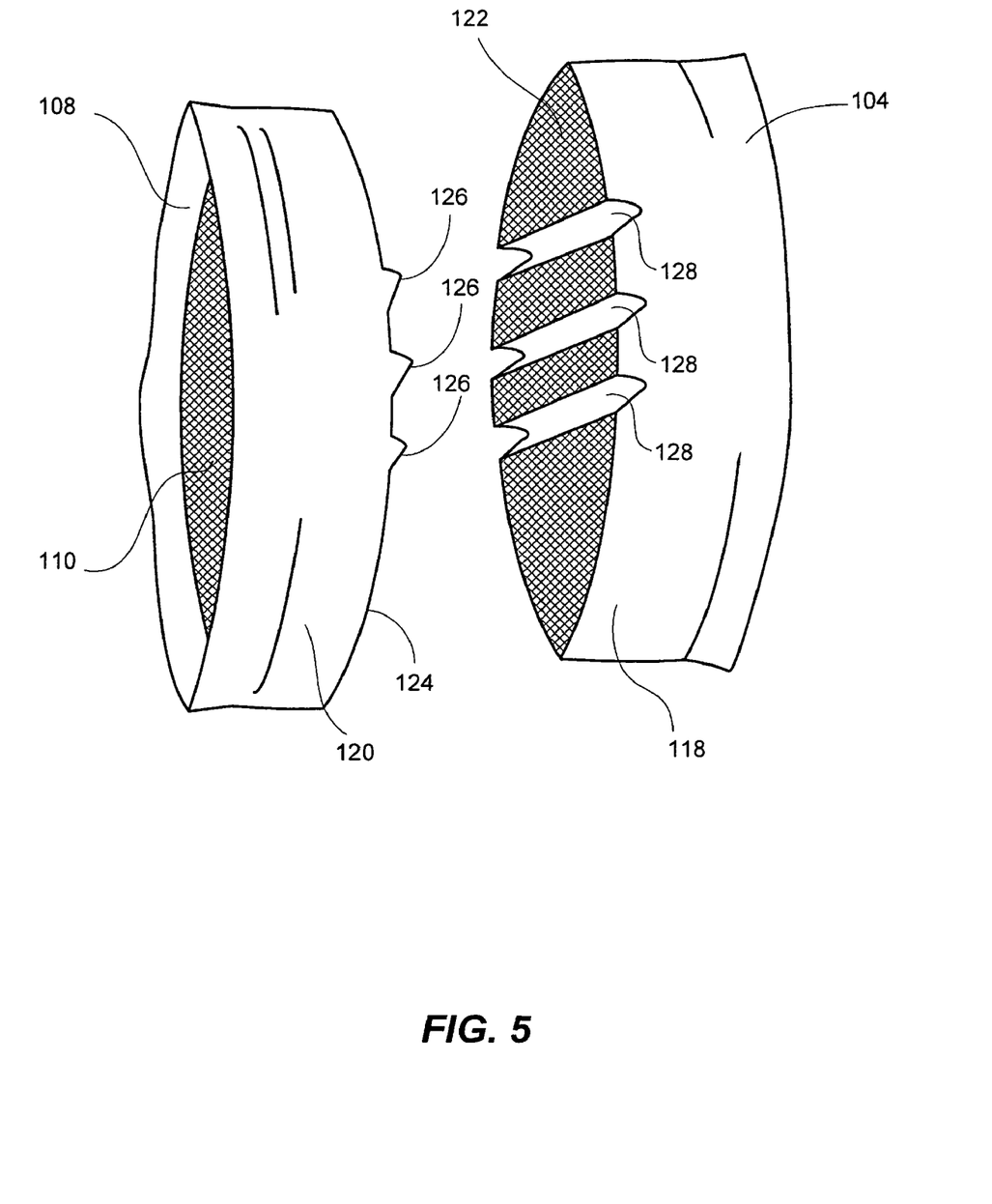
FIG. 5 is a perspective view of the upper and lower disc halves of FIG. 4, showing exemplary lock-and key features bottom perspective view of the self-retaining spinal disc of FIG. 1.

FIG. 5 shows lower half-disc 120 with extrusions 126 of its joining surface 124. Extrusions 126 mate with complementary recesses 128, formed in bottom surface 122 of upper half-disc 118. Extrusions 126 and recesses 128 or other lock-and-key features may be scored, carved, melted or otherwise formed in upper and lower half-discs 118, 120, for example when one mold is used to form both disc halves. Alternately, paired molds with complementary features or texture on their inner, bottom surfaces may be used to form upper and lower half-discs 118, 120 with complementary top and joining surfaces 122, 124, respectively.

Figure 6:
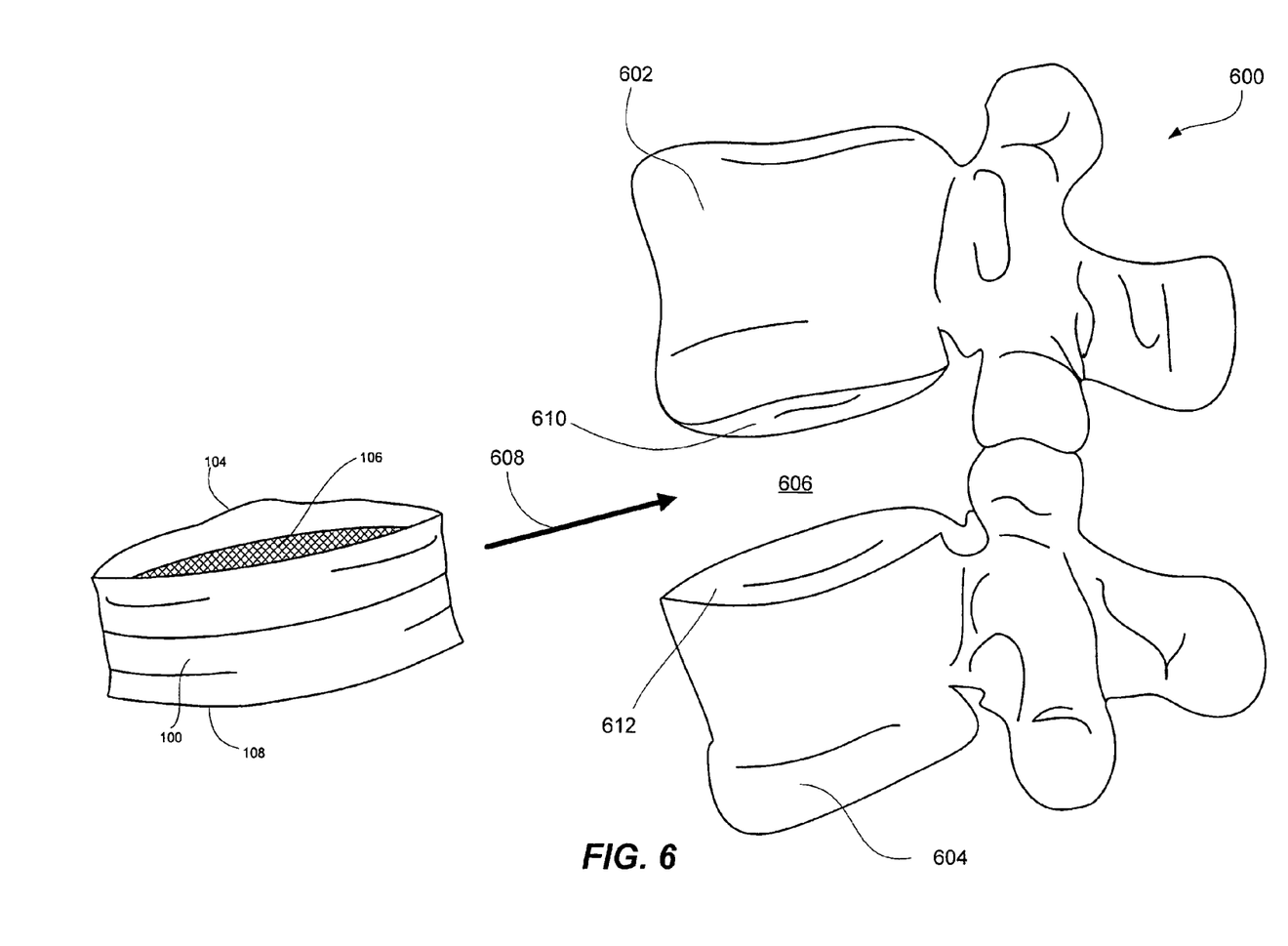
FIG. 6 depicts insertion of the artificial spinal disc of FIGS. 1 and 2 into a spinal segment.

FIG. 6 illustrates insertion of a self-retaining artificial spinal disc (e.g., disc 100) in a recipient's spinal column. In particular, FIG. 6 depicts an exemplary spinal segment 600 with upper and lower vertebral bodies 602, 604. Vertebral body 602 is cranially adjacent, and vertebral body 604 caudally adjacent, to an intervertebral space 606. The natural disc which would occupy the intervertebral space 606 between bodies 602, 604 has been surgically removed in preparation for implanting self-retaining artificial spinal disc 100. Disc 100 is inserted between vertebral bodies 602, 604, as indicated by motion arrow 608, for example by compressing (e.g., squeezing) the disc slightly and inserting it between bodies 602, 604 or in some instances by separating vertebral bodies 602, 604 slightly prior to inserting disc 100. Disc 100 is inserted such that superior disc body face 106 rests against and contours to a lower face 610 of upper vertebral body 602 and inferior disc body face 110 (see, e.g., FIG. 5) rests against and contours to an upper face 612 of lower vertebral body 604.

Figure 7:
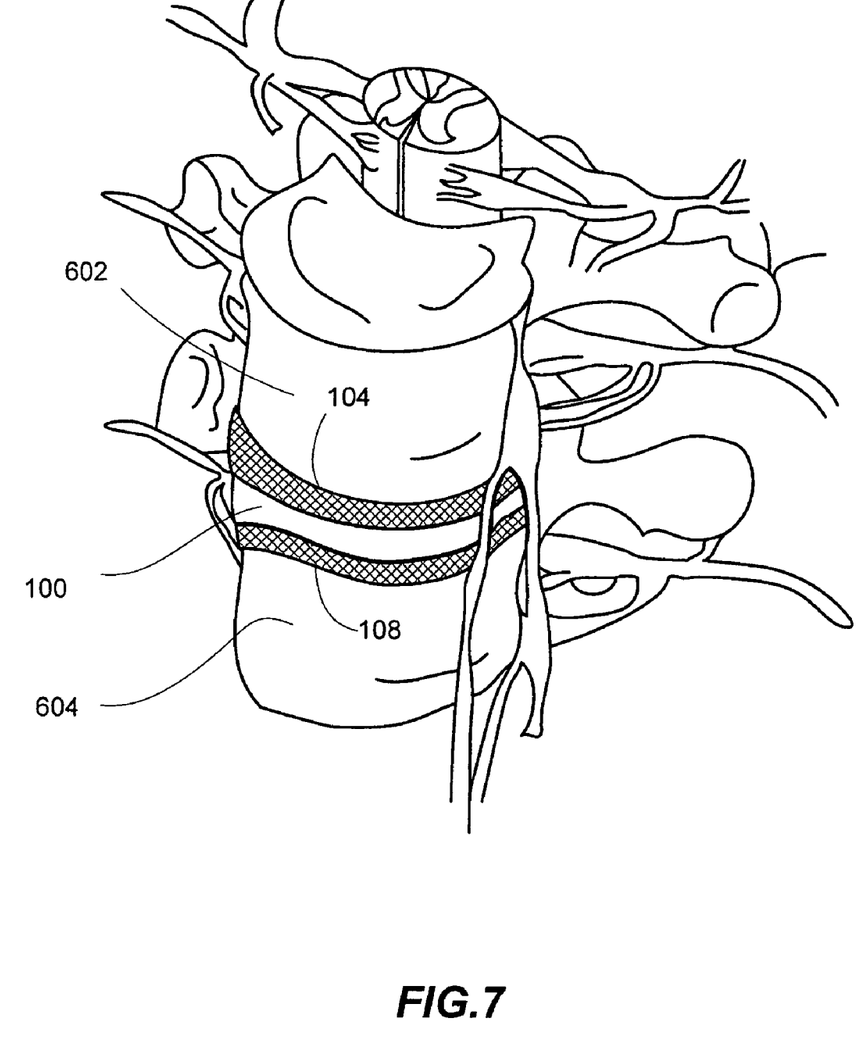
FIG. 7 is a schematic illustration of the artificial spinal disc of FIG. 6 seated within a spinal segment.

Meniscus 104 encircles and overlies a bottom portion of vertebral body 602 and meniscus 108 encircles and overlies a top portion of vertebral body 604, as shown in FIG. 7. During insertion, menisci 104, 108 are manipulated around the vertebral bodies, for example by stretching the menisci outward and upward/downward while progressively working around vertebral bodies 602, 604. Once in place, menisci 104, 108 snugly fit to vertebral bodies 602, 604. Menisci 104, 108 may additionally be formed with texture (e.g., using a shaping device as described in method 300) to further enhance gripping of vertebral bodies 602, 604.

FIG. 7 schematically depicts disc 100 seated between adjacent vertebral bodies 602, 604 of spinal segment 600. Disc 100 is for example manufactured to fit where the recipient's natural disc was positioned prior to damage or degeneration. When disc 100 is correctly inserted, superior and inferior faces 106, 110 fit snugly against vertebral faces 610, 612 (i.e., without substantial gaps therebetween). Menisci 104, 108 (shown with cross-hatching for clarity) overlie the adjacent vertebral bodies and may frictionally retain the disc in place and/or aid in creating a retaining suction seal between disc 100 and the adjacent vertebrae. Because the meniscus retains the disc in place, the need for additional mechanical devices to seat or retain the disc may be eliminated, and invasiveness and complications of disc replacement surgery reduced.

Over time, tissue ingrowth enhances the stability of disc 100. Preliminary studies particular to the disc show that, once in place, it is quite difficult to remove from between the vertebra.

While the present invention has been described above, it should be clear that many changes and modifications may be made to the process and product without departing from the spirit and scope of this invention.

What is claimed is:

1. A self-retaining artificial spinal disc comprising:
   a disc body formed of a flexible material and having a superior surface and an opposed inferior surface, the disc body sized to fit an implant site between a caudally adjacent vertebral body and a cranially adjacent vertebral body of an existing human spine;
   a superior meniscus formed as a continuous peripheral extension of the flexible material of the superior surface and configured to encircle a portion of the cranially adjacent vertebral body; and
   an inferior meniscus formed as a continuous peripheral extension of the flexible material of the inferior surface and configured to encircle a portion of the caudally adjacent vertebral body;
   wherein the superior meniscus and the superior surface are operable to form a suction seal with the encircled portion of the cranially adjacent vertebral body and the inferior meniscus and the inferior surface are operable to form a suction seal with the encircled portion of the caudally adjacent vertebral body, to retain the artificial spinal disc in place post-surgery, without mechanical fasteners.

2. The self-retaining artificial spinal disc of claim 1, the flexible material comprising silicone.

3. The self-retaining artificial spinal disc of claim 1, the flexible material comprising an elastomer.

4. The self-retaining artificial spinal disc of claim 3, the elastomeric disc body comprising one or both of:
   pores for facilitating tissue in-growth, and
   infused antibiotic, anti-rejection or anti-inflammatory drugs.

5. The self-retaining artificial spinal disc of claim 1, wherein the superior and inferior menisci include texture for enhancing grip of the encircled portions of the cranially and caudally adjacent vertebral bodies.

6. The self-retaining artificial spinal disc of claim 1, the superior and inferior surfaces including contours for fitting faces of the cranially and caudally adjacent vertebral bodies.

7. The self-retaining artificial spinal disc of claim 1, the disc body having a size and a characteristic of a natural occurring vertebral disc.

8. The self-retaining artificial spinal disc of claim 7, the characteristic comprising hardness, weight, tensile strength, compressibility, flexibility, void volume and/or porosity.

9. A self-retaining artificial spinal disc, comprising:
   an upper half-disc formed of a flexible material and having an inferior surface, a superior surface and a superior meniscus formed as a peripheral extension of the flexible material of the superior surface; and
   a lower half-disc formed of the flexible material and comprising:
      a joining surface for joining to the inferior surface of the upper half-disc, and
      an inferior meniscus formed as a peripheral extension of the flexible material on a side opposite the joining surface;
   wherein the superior meniscus and the superior surface are operable to form a vacuum seal with a first vertebral body adjacent an implant site and the inferior meniscus and the inferior surface are operable to form a vacuum seal with a second vertebral body adjacent the implant site and opposite the first vertebral body, to retain the artificial spinal disc in place post-surgery, without mechanical fasteners, when the upper and lower half discs are joined.

10. The self-retaining artificial spinal disc of claim 9, wherein the inferior surface of the upper half-disc and the joining surface of the lower half-disc are flat.

11. The self-retaining artificial spinal disc of claim 9, wherein the inferior surface of the upper half-disc and the joining surface of the lower half-disc comprise lock and key features, for fitting the half-discs together.

12. The self-retaining artificial spinal disc of claim 9, wherein the superior surface of the upper half-disc comprises contours for fitting surface features of the first vertebral body.

13. The self-retaining artificial spinal disc of claim 9, wherein the side of the lower half-disc opposite the joining surface comprises contours for fitting with surface features of the second vertebral body.

\* \* \* \* \*